United States Patent [19]
Batchelder et al.

[11] Patent Number: 5,192,870
[45] Date of Patent: Mar. 9, 1993

[54] OPTICAL SUBMICRON AEROSOL PARTICLE DETECTOR

[75] Inventors: John S. Batchelder, Somers; Donald M. DeCain, New York; Philip C. D. Hobbs, Briarcliff Manor, all of N.Y.

[73] Assignee: International Business Machines Corporation, Armonk, N.Y.

[21] Appl. No.: 820,709

[22] Filed: Jan. 14, 1992

[51] Int. Cl.⁵ .......................................... G01N 15/06
[52] U.S. Cl. .................................... 250/574; 356/28.5
[58] Field of Search .............. 250/573, 574, 575, 225; 356/28.5, 28, 336, 338, 342, 343

[56] References Cited

U.S. PATENT DOCUMENTS

| | | | |
|---|---|---|---|
| 4,365,896 | 12/1982 | Mihalow | 356/446 |
| 4,373,807 | 2/1983 | Gouesbet | 356/28.5 |
| 4,492,467 | 1/1985 | Drain et al. | 356/336 |
| 4,737,652 | 4/1988 | Faschingleitner et al. | 250/575 |
| 4,986,659 | 1/1991 | Bachalo | 356/336 |
| 4,997,272 | 3/1991 | Dopheide et al. | 356/28.5 |
| 5,047,653 | 9/1991 | Garcia et al. | 250/574 |

*Primary Examiner*—David C. Nelms
*Attorney, Agent, or Firm*—Perman & Green

[57] ABSTRACT

A particle detector that determines the presence of particles in an enclosed volume includes a laser that directs a coherent optical beam to a beam splitter that produces first and second divergent beams. An optical system images the point of origin of the two divergent beams within the beam splitter into the enclosed volume, whereby the first and second beams are caused to intersect and interfere at an inspection region within the volume. A detector is positioned adjacent the volume and is responsive to light scattered from one of the beams, as a result of a particle passing through the inspection region, to produce an electrical signal indicative of the intensity of the scattered light. A signal processor analyzes the electrical signals and to determine the presence of the particle. An embodiment of the invention includes an acousto-optic modulator to enable one of the beams to be frequency shifted from the other beam so as to enable the presence of a carrier signal on which a particle's Doppler frequency is modulated. Another embodiment relies upon the Doppler modulation of a reflected optical beam to create an interference pattern at a detector.

16 Claims, 4 Drawing Sheets

OPTICAL SUBMICRON AEROSOL PARTICLE DETECTOR

FIELD OF THE INVENTION

This invention relates to the sensing of submicron particles and, more particularly, to the sensing of such particles in a chamber or volume.

BACKGROUND OF THE INVENTION

Instruments for detecting and counting particles are essential process control tools in semiconductor and semiconductor package manufacturing. Most such instruments employ a sampling technique where a small amount of fluid (e.g. a gas or a liquid) from a volume under test is drawn through an active region of a counter and the particles in the sample are counted. Provided flow rates are known and no particles are lost or gained from the sampling tube walls, these instruments yield reasonably accurate estimates of particle concentrations. In certain cases, however, it may not be possible to sample volumes of fluid from within an enclosure for particle concentrations. Examples of such volumes are vacuum chambers (where there is no fluid to sample) and furnaces where the insertion of sampling probes may be impractical. A sampling process may also produce misleading results where the total fluid volume is small (e.g., inside magnetic disk drives) so that the sample flow becomes large compared to the usual air exchange This will result in erroneously low particle counts being indicated The prior art illustrates a number of optical systems for remote detection of microscopic particles U.S. Pat. No. 4,737,652 to Faschingleitner et al. illustrates an optical system wherein reference and test beams are passed through a test volume, chopped and then detected to determine the presence of particles in the test beam. By passing the reference beam through a similar environment as the test beam, common mode noise and other perturbations of the test beam can be eliminated.

In U.S. Pat. No. 4,492,467 to Drain et al., a system for determining the size of spherical particles is described wherein back-scattered, circularly polarized light, reflected from a particle, is assessed. The system measures the angular intensity distribution of the back-scattered light and converts it to particle size.

In U.S. Pat. No. 4,365,896 to Mihalow, a system is disclosed for correcting for optical attenuation that occurs in a beam used to interrogate an enclosed volume.

Bachalo in U.S. Pat. No. 4,986,659, describes a method for measuring the size and velocity of microscopic particles, using the phase and intensity of scattered light. The Bachalo system is similar to a phase-Doppler velocimeter wherein a pair of coherent, identical frequency optical beams are caused to cross within a volume being examined, to create an interference pattern at the crossing point. By examining particle-scattered light from the region of interference, the presence of the particle is detected. Bachalo indicates that the scattered light is directed onto photo detectors that enable the phase of a Doppler burst to be detected. In addition, the amplitude of the Doppler burst is detected to enable a sizing of the particle.

A similar system to that described by Bachalo is shown in U.S. Pat. No. 4,373,807 to Gouesbet. However, one of the crossing beams has its frequency acousto-optically altered by a Bragg cell. As a result, the interference pattern created by the crossing beams exhibits fringe movement at the beat frequency between the beams, such that presence of a particle therein results in a signal offset from the beat frequency by the Doppler frequency. Both Bachalo and Gouesbet achieve their dual beams through the use of a beam splitter and require very precise alignment of their systems to achieve a prescribed beam crossing region.

Accordingly, it is an object of this invention to provide a submicron particle detector which eliminates the need for high precision optical system alignment.

It is another object of this invention to provide an improved optical particle detection system that is able to discriminate between weak signals from particles and much stronger ones from surface scatter and other stray light.

It is still another object of this invention to provide improved optical detection systems that can operate with forward and back-scattered optical energy.

SUMMARY OF THE INVENTION

A particle detector that determines the presence of particles in an enclosed volume includes a laser that directs a coherent optical beam to a beam splitter which produces first and second beams that diverge from each other. An optical system images the point of origin of the two divergent beams (within the beam splitter) into the enclosed volume, whereby the first and second beams are caused to intersect and interfere at an inspection region within the volume. A detector is positioned adjacent the volume and is responsive to light scattered from one of the beams by a particle passing through the inspection region, to produce an electrical signal indicative of the intensity of the scattered light. A signal processor analyzes the electrical signal and determines the presence of the particle.

An embodiment of the invention includes an acousto-optic modulator to enable one of the beams to be frequency shifted from the other beam so as to enable the presence of a carrier signal on which a particle-induced Doppler frequency is modulated. Another embodiment relies upon Doppler modulation of back-scatter from a particle to create an interference pattern at a detector.

DETAILED DESCRIPTION OF THE INVENTION

Figures 1, 2:
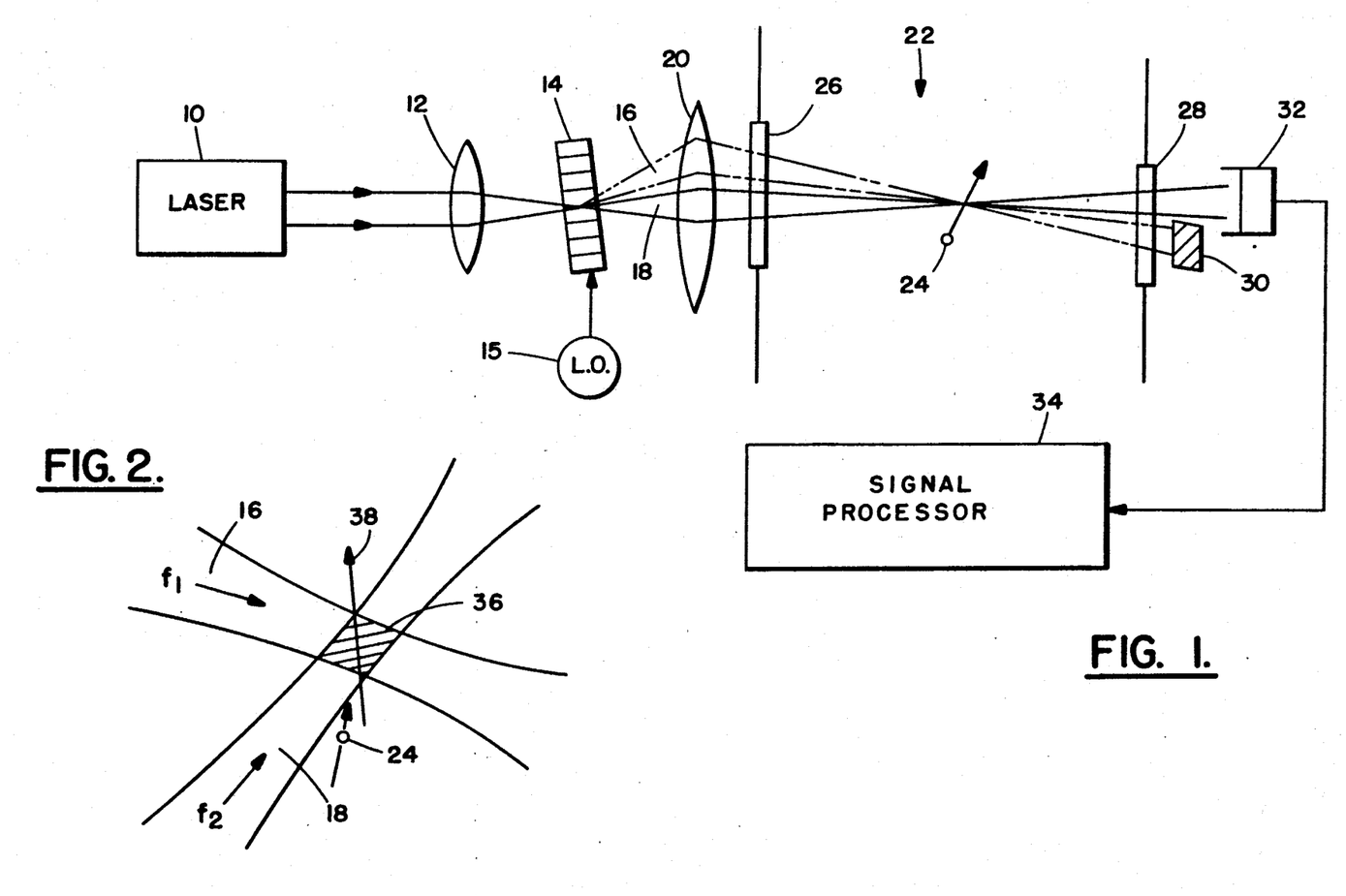
FIG. 1 is a schematic diagram of a particle detector embodying the invention hereof.
FIG. 2 is a diagram showing the interference pattern created by the crossing of the optical beams in the system of FIG. 1.

Referring to FIG. 1, an optical system is shown that uses forward-scatter to determine the presence of a particle in an enclosed volume. A laser 10 generates a polarized optical beam which is focused by a lens 12 onto a beam splitter 14. The preferred embodiment shown in FIG. 1 employs heterodyne principles, so beam splitter 14 is an acousto-optic device such as a Bragg cell.

Bragg cell 14 upon application of a signal from a local oscillator 15, creates a divergent beam 16 (in addition to transmitted beam 18) whose frequency is modulated by the signal applied by local oscillator 15. Thus, if the frequency of local oscillator 15 is 80 MHz, then the optical frequency of beam 16 differs from the optical frequency of beam 18 by 80 MHz.

Beams 16 and 18 are focused by lens 20 through window 26 into enclosed volume 22 wherein a particle (or particles) 24 are present. Lens 20 is positioned so as to image the point of origin of beam 16 within Bragg cell 14 into volume 22. By utilizing lens (or lenses) 20 to image the point of origin of beam 16, the alignment problem present in the prior art is eliminated due to the fact that beams 16 and 18 will invariably cross at a known point within volume 22, solely in dependence upon the focal distance of lens 20. It is preferred that the beam from laser 10 be focused at the center of Bragg cell 14 in order for the overlap region of beams 16 and 18 (within volume 22) to encompass the beam foci. Since the angular acceptance of Bragg cell 14 is likely to be relatively small, the focusing is generally weak and the depth of focus is large. Therefore, the positioning of the focus in the Bragg cell is easily accomplished. The numerical aperture in the intersection region of beams 16 and 18 can be as large as desired.

After passing through the intersection region, beams 16 and 18 pass through a window 28, with beam 16 being absorbed in a beam dump 30 and beam 18 being directed onto a photocell 32. The output from photocell 32 is fed to a signal processor 34 that enables the presence of a particle 24 to be indicated.

Referring to FIG. 2, beams 16 and 18 are shown at their point of intersection within volume 22. Since beam 16 differs in frequency from beam 18 by the modulating frequency applied to Bragg cell 14, a moving fringe pattern 36 is produced at the intersection of the beams. The fringes move in the direction shown by arrow 38 at a rate determined by the frequency of modulating oscillator 15. Thus, when a particle 24 enters intersection region 36, movement of the particle through the moving fringe pattern induces a Doppler shifted burst in the optical frequency of beam 18. The amount of Doppler shift is related to the velocity of particle 24 as it passes through intersection region 36. Photocell 32 is responsive to the forward scattered burst of optical energy to produce an electrical signal having frequency components that encompass the modulating frequency of local oscillator 15 plus and minus the largest expected Doppler shift created by particle 24.

Figure 3:
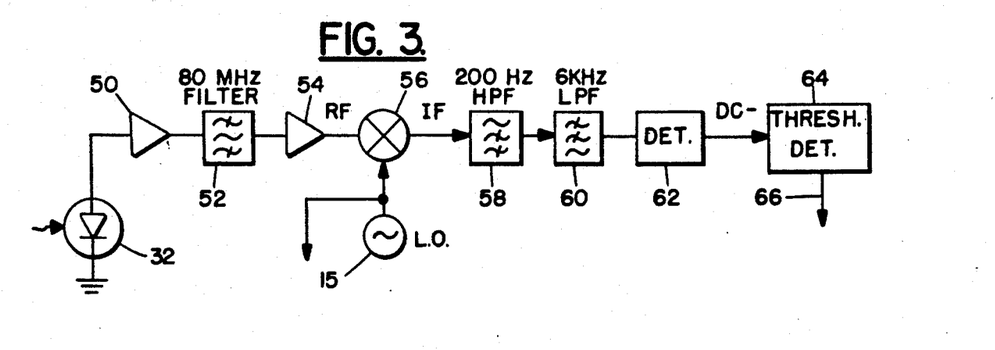
FIG. 3 is a first embodiment of a signal processor for detecting the presence of a submicron-size particle in the system of FIG. 1.

In FIG. 3, a schematic is shown of one embodiment of circuitry within signal processor 34. Photocell 32 feeds its output to an amplifier 50, whose output is, in turn, fed through a band pass filter 52. In this instance, it is assumed that the local oscillator frequency is 80 MHz, thus the center frequency of filter 52 is also 80 MHz. The output from filter 52 is amplified in amplifier 54 and passed to a mixer 56, which also has applied the 80 MHz modulating signal from local oscillator 15. That is the same signal that is applied to Bragg cell 14. As a result, the output from mixer 56 is a base band beat frequency including the Doppler tone burst envelope created when particle 24 passes through intersection region 36. The Doppler tone burst is passed through a 200 Hertz high pass filter 58 that removes DC, and other slowly varying levels that result from reflections off of the walls of volume 22 and windows 26 and 28, as well as electronic offsets and drift.

The output from filter 58 is then fed to a low pass filter 60 (6 KHz) that sets the detection bandwidth of the system and eliminates extraneous noise outside that bandwidth. The filtered signal is then detected in detector 62 and fed, as a base band signal, to threshold detector 64. If the base band signal's instantaneous level exceeds a preset threshold within threshold detector 64, an output appears on line 66 indicating the presence of a particle.

Figure 4:
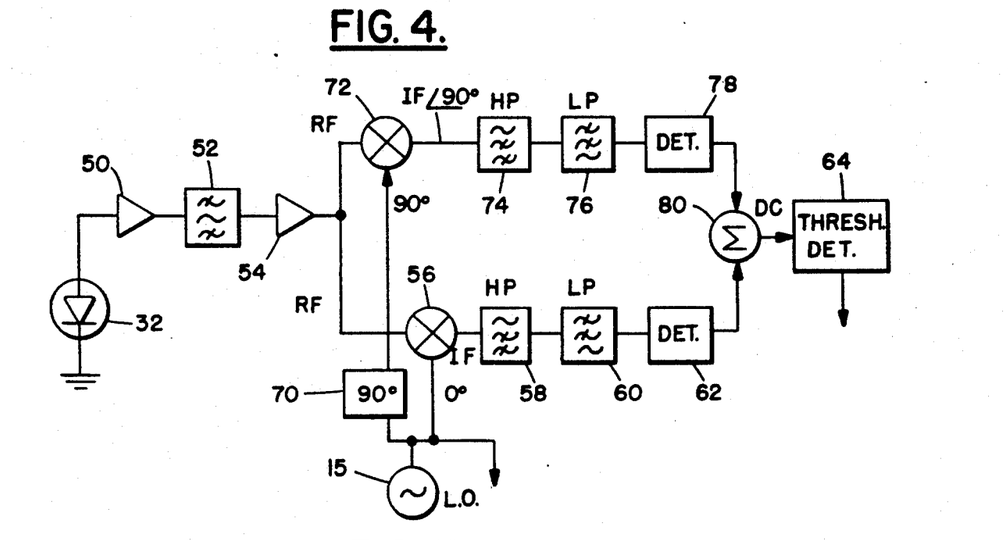
FIG. 4 is a second embodiment of a signal processor for detecting the presence of a submicron-size particle in the system of FIG. 1.

Turning to FIG. 4, another signal processor embodiment is shown that enables reduction of envelope ripples from the Doppler tone burst. In FIG. 4 the circuit of FIG. 3 has been augmented by adding an additional channel wherein the local oscillation signal is displaced by 90° from the local oscillator signal fed to mixer 56. To create the phase shifted local oscillator signal, the output from local oscillator 15 is passed through a 90° phase shifter before being applied to a mixer 72, connected in parallel to mixer 56. The resulting phase shifted beat frequency (the envelope shape is not phase shifted) is applied to filters 74, 76 and detector 78 (identical to filters 58, 60 and detector 62). The outputs of detectors 62 and 78 are combined in summer 80 and then applied to threshold detector 64. The summing, after full wave rectification, of two identical Doppler tone bursts (with the carrier for one shifted by 90° from the other), achieves a substantial reduction in Doppler envelope ripple (an RMS summer can further reduce envelope ripple). As a result, the output from threshold detector 64 exhibits more accurate detection of particles in the beam intersection region.

The system of FIG. 1 can also be operated as a homodyne system, with Bragg cell 14 being replaced by a beam splitter. In this instance, the signal detected by photocell 32 is the Doppler frequency created as a result of the interaction between particle 24 and a set of stationary interference fringes The circuitry within signal processor 34 is modified by the exclusion of band pass filter 52 and mixer 56. In other respects, the signal processor circuitry is similar to that shown in FIG. 3. A detection system which uses a beam splitter, in lieu of an acousto-optic modulator, does exhibit drawbacks (e.g. sensitivity to stray light, 60 Hz pick-up and microphonics).

Figures 5, 6:
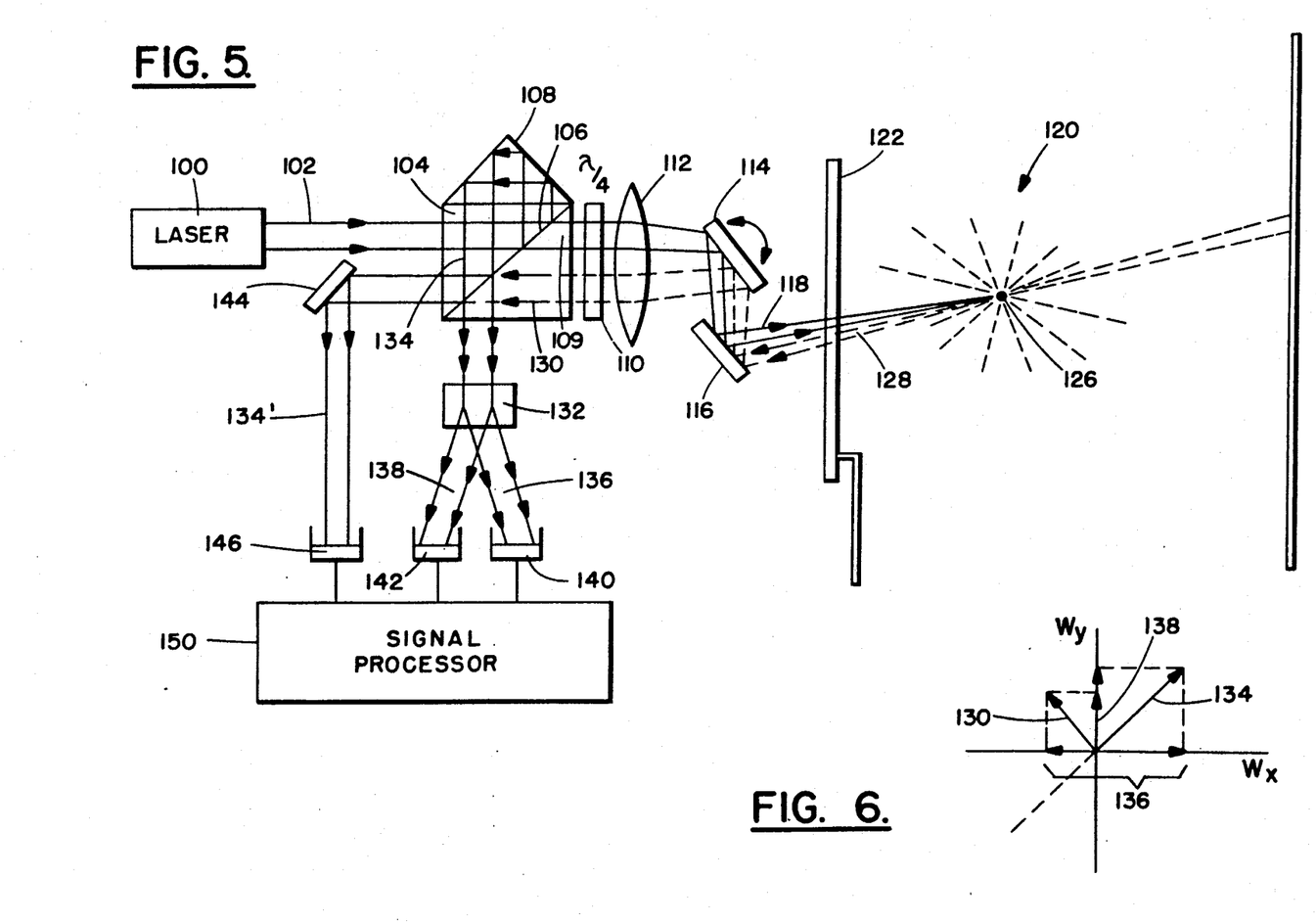
FIG. 5 is a block diagram of another embodiment of a particle detector that incorporates the invention hereof, this embodiment relying upon back-scattered optical energy.
FIG. 6 is a phasor diagram showing polarization states of optical beams and the optical axes of a Wollaston prism on which the optical beams are incident in the system of FIG. 5.

Turning to FIG. 5, a particle detector embodiment is shown which relies upon reflected scattered light from a particle in an enclosed volume. Laser 100 produces a highly polarized beam 102 that is directed at a polarizing beam splitter (PBS) 104. The direction of polarization of beam 102 has a component orthogonal to the polarization angle of polarizing surface 106 so that a small portion of beam 102 is reflected towards a dielectric retro-reflector 108. The remainder of beam 102 is unhindered by surface 106 and passes as beam 109 to quarter wave plate 110, whose orthogonal axes are oriented at 45° to the angle of polarization of beam 109. As a result, the beam exiting from quarter wave plate 110 is circularly polarized and exhibits a helicity that is either right handed or left handed.

The thus circularly polarized beam passes through a lens 112 and is reflected by a pair of scanning mirrors 114 and 116 (which create a raster scan) to create beam 118 which enters volume 120 through window 122. If particles within volume 120 are moving sufficiently rapidly one or both of scanning mirrors 114 and 116 can be eliminated and the beam directly introduced into the volume.

If a particle 126 passes through scanned beam 118, a Doppler shift is imposed upon the reflected scattered light that is directed back in the direction shown by dotted beam 128. Due to the reflection, the direction of helicity of beam 128 is reversed from that of beam 118. When beam 128 thus encounters quarter wave plate 110, the resulting beam that exits therefrom (beam 130) is linearly polarized, but oriented at an angle that is orthogonal to beam 109. Beam 130 is thus reflected by polarizing surface 106 in a downward direction towards a Wollaston prism 132. Those skilled in the art will realize that the other polarizing beam splitters can be substituted for Wollaston prism 132.

In the meanwhile, retro reflector 108 has caused the small portion of incident beam 102 that was reflected upwardly by PBS 104 to be reflected back (anti-parallel to itself) as beam 134. If beam 134 had exactly the same polarization as incident beam 102, it would be entirely reflected by polarizing surface 106. Retro reflector 108, however, operates by forcing retro reflected beam 134 to undergo three successive total internal reflections from orthogonal surfaces. Since the phase shift during internal reflection depends upon angle and polarization, the polarization of beam 134 can be adjusted over a large range by rotating retro reflector 108 about its three fold symmetry axis. This results in an adjustable fraction of retro reflected beam 134 being transmitted through polarizing surface 106 towards Wollaston prism 132.

As above indicated, beam 130 exhibits one angle of linear polarization while beam 134 exhibits an orthogonal direction of polarization, both beams combining and interfering at Wollaston prism 132. In FIG. 6, the orthogonal polarization phasors of beams 130 and 134 are illustrated. The axes of Wollaston prism 132 are oriented near 45° with respect thereto and are designated as $W_y$ and $W_x$, respectively. Wollaston prism 132 thus directs at photo detector 140, a beam 136 that has an instantaneous intensity that is represented by the squared modulus of the vector sum of the projections on the $W_x$ axes of the phasors representing beams 130 and 134. Similarly, Wollaston prism 132 directs a beam 138 towards photo detector 142, beam 138 having an instantaneous intensity value that varies in accordance with the projections of polarization phasors of beams 130 and 134 on the $W_y$ axis. An examination of FIG. 6 will show that the intensities of beams 136 and 138 vary in opposite senses as a result of changes in phase and amplitude of beams 130 and 134. Thus, the projections of beams 130 and 134 onto the $W_x$ axis subtract whereas their projections onto the $W_y$ axis are additive, thereby creating opposing direction changes in intensity on photo detectors 140 and 142.

In addition to the interference signals produced by photo detector 140 and 142, an additional signal is employed to remove laser noise from the interference signals. As above indicated, the polarization state of reflected beam 134 (FIG. 5) can be adjusted by the rotation of retro reflector 108. By causing the angle of polarization of beam 134 to be somewhat divergent from the direction of polarization of inclined surface 106, a portion of beam 134 is reflected towards a mirror 144 and from there, as beam 134' to a third photo detector 146. The signal from photo detector 146, as will be hereinafter understood, is employed in signal processor 150 in a differential manner to remove laser noise from the outputs of photo detectors 140 and 142.

Figure 7:
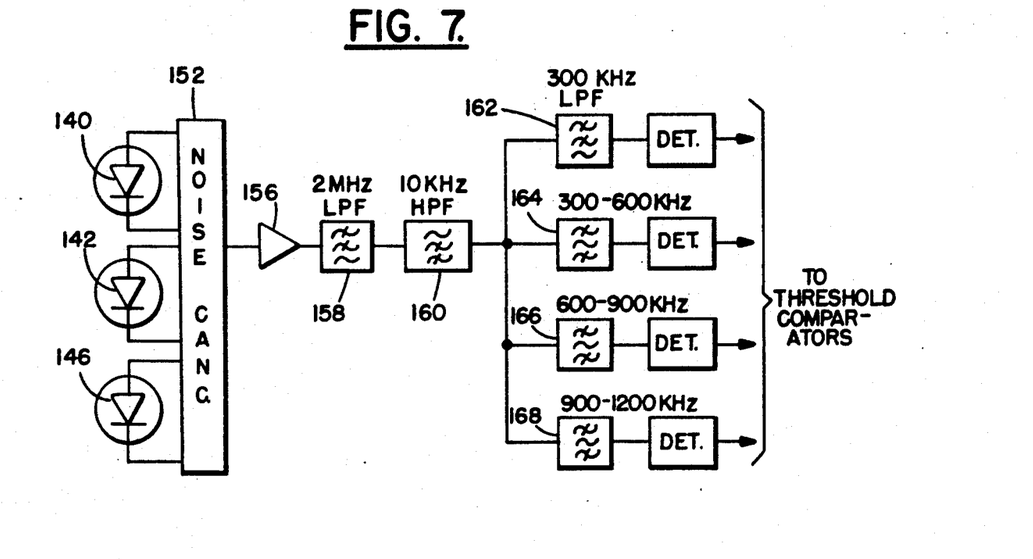
FIG. 7 is a signal processor for enabling the detection of a submicron-size particle in the system of FIG. 5.

In FIG. 7, a block diagram illustrates the major components that enable signal processor 150 to indicate the presence of a particle or particles within volume 120. The back scattering system shown in FIG. 5 can result in large Doppler shifts being induced in reflected beam 128. This is due to the fact that a particle moving radially along the direction of incident beam 118 can create a Doppler shift as large as 2 MHz, at expected particle velocities. This is contrasted to Doppler shifts for the system of FIG. 1 that are in the 10 KHz frequency range. This can better be understood by realizing that the Doppler shift frequency is proportional to 2 Sin $\theta_s/2$, where $\theta_s$ is the angle between the incident beam and the particle-scattered beam. For a forward scatter angle of approx. 0.5°, the value of the Sin function is 0.01 and for a back scatter of 180°, the value of the Sin function is 2. Thus there is a 200× larger Doppler shift for the back scatter system.

As a result of the large Doppler frequency range in the system of FIG. 5, sensitivity advantages can be gained by splitting the expected Doppler signal bandwidth into smaller bands, roughly the same width as the transit time bandwidth, and detecting tone bursts in each band separately.

In FIG. 7, photo detectors 140, 142 and 146 feed their respective signals into noise cancelling circuit 152. A portion of the current from photo detector 146 is subtracted from the difference of the currents derived from photo detectors 140 and 142 to thereby reduce the laser noise present therein. The resulting signal is then amplified in amplifier 156 and passed through filters 158 and 160. Filter 158 sets the upper bandwidth limit of the detection circuit, and filter 160 removes low frequency components from the Doppler signal. This is important as the scanning of beam 118 by mirrors 114 and 116 (FIG. 5) causes considerable speckle to be fed back into the system as the result of reflections from the rear wall of volume 120. Those signals are at a low frequency (compared with the transit-time bandwidth and Doppler shifts of most particles) and are eliminated by filter 160.

The filtered Doppler signal is then broken into a plurality of frequency bands by filters 162, 164 and 166 and 168. The output from each filter is detected and fed to a threshold comparator in the manner shown in FIGS. 3 and 4. Thus, depending upon where in the dynamic range the Doppler signal resides, one of the aforementioned filters isolates and detects the Doppler tone burst envelope and feeds the detected envelope to a threshold comparator to enable the determination of the presence of a particle or particles within volume 120.

Figures 8, 9:
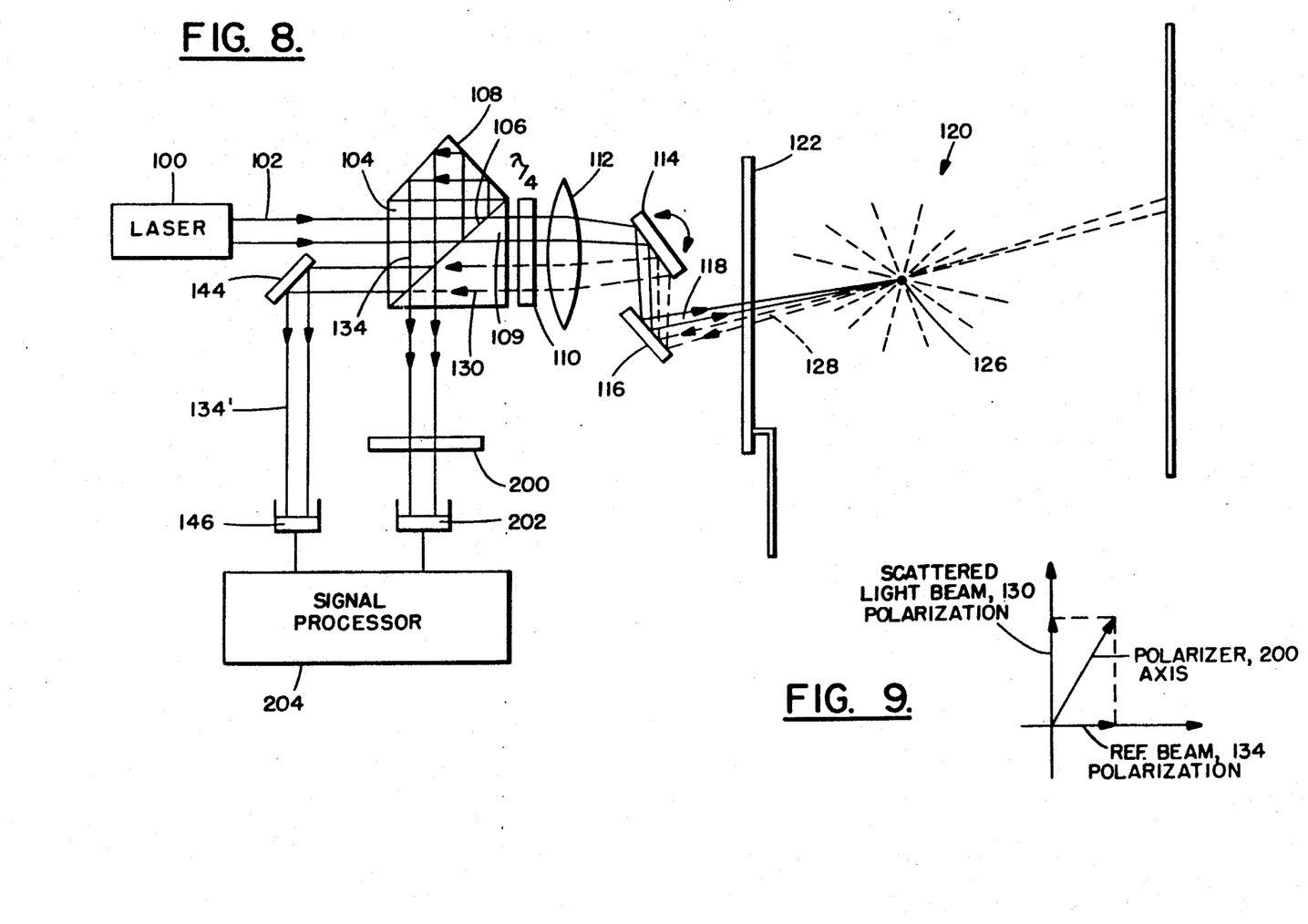
FIG. 8 is another embodiment of a back-scatter particle detector embodying the invention hereof.
FIG. 9 is a phasor diagram helpful in understanding the operation of FIG. 8.

In lieu of using Wollaston prism 132 to make reference beam 134 and scattered beam 130 interfere, a polarizer may be used whose axis is oriented at an angle to the polarization vectors of the two beams. Referring to FIGS. 7 and 8, a polarizer 200 is shown oriented nearly along the polarization axis of the scattered light (see FIG. 8). Such an orientation allows most of the scattered light to pass through the polarizer 200 to detector 20, minimizing the degradation in signal-to-noise ratio which results from the loss of scattered photons. This orientation causes polarizer 200 to absorb most of the light in reference beam 134; however, since reference beam 134 contains only a small part of the total laser power, increasing its strength to compensate for the loss in the polarizer does not appreciably decrease the sensitivity of the system. However, the increase of laser power does add expense to the system. Signal processor 204 is substantially identical to that shown in FIG. 7 except that one photodetector input to noise canceller 152 is eliminated.

It will be appreciated by those skilled in the art that the particle detector of FIG. 1 has been described in both heterodyne and homodyne versions. The particle detectors of FIGS. 5 and 8 are shown in a homodyne version; however, they also can be operated in the heterodyne manner through the inclusion of an appropriate acousto-optic modulation means and local oscillator. The signal processor will also require demodulation circuitry to remove the modulation signal and produce intermediate frequency signals containing the desired Doppler tone bursts.

The systems of FIGS. 1, 5 and 8 can also be employed to obtain an indication of particle size. When a particle crosses the interaction region in either of the embodiments, it produces a burst of scattered light at a photocell, with the photocell, in turn, producing a pulse or tone burst whose duration is the transit time of the particle. For a given particle trajectory, the amplitude of the pulse is a measure of the particle size. Therefore, the particles can be sorted into size categories using pulse height analysis. The curve relating burst signal amplitude to particle size is monotonic in the case of the forward scattered light system shown in FIG. 1. However, for the systems of FIGS. 5 and 8, back-scattered light exhibits resonances which render its curve less predictable. Nevertheless, size binning by amplitude measurement is useful even in the systems of FIGS. 5 and 8 as long as it is remembered that there will be a few large particles which look like small particles because of resonances.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

We claim:

1. A particle detector for detecting particles within an enclosed volume, the detector comprising:
   beam splitter means;
   laser means for directing a coherent optical beam along a path to said beam splitter means, said beam splitter means splitting said coherent optical beam into at least first and second beams, the first beam deflected from the path of said second beam, both said first and second beams having a point of origin in the vicinity of said beam splitter means;
   optical means for imaging said point of origin into said enclosed volume, whereby said first and second beams are caused to cross and interfere at an interaction region within said enclosed volume;
   detector means responsive to at least one said beam for sensing optical energy scattered by a particle's passage through said interaction region, said particle creating a Doppler shifted burst in said optical energy, said detector means producing an electrical signal including a Doppler tone burst analogue of said Doppler shifted burst; and means for processing said electrical signal to determine the presence of said particle in said interaction region.

2. The particle detector as recited in claim wherein said optical means images said first and second beams through one portal in said enclosed volume and said detector means is positioned to detect forward scattered optical energy that passes outside said enclosed volume through another portal.

3. The particle detector as recited in claim wherein said processing means includes filter means for isolating said Doppler tone burst and threshold means for determining if an envelope of said Doppler tone burst exceeds a preselected limit and indicates the presence of a particle.

4. A particle detector for detecting particles within an enclosed volume, said particle detector comprising:
   a modulation frequency source of frequency f;
   acousto-optic (A/0) means connected to said modulation frequency source;
   laser means for directing a coherent optical beam along a path to said A/O means, said A/O means splitting said coherent optical beam at a point of origin into at least first and second optical beams, said first optical beam exhibiting a frequency that is offset from the frequency of said second optical beam by the frequency of said modulation frequency source, said first optical beam deflected by said A/0 means from the path of said second optical beam;
   optical means for imaging said point of origin into said enclosed volume, whereby said first and second optical beams are caused to intersect and interfere at an interaction region within said enclosed volume;
   detector means responsive to scattered optical energy that results when a particle passes through said interaction region, for sensing a Doppler shifted light burst therein and producing an electrical signal that includes a Doppler tone burst analogue of said Doppler shifted light burst; and
   means for processing said electrical signal to extract the Doppler tone burst's envelope to enable determination of the presence of a particle in said interaction region.

5. The particle detector as recited in claim wherein said detector means is positioned to detect forward scattered optical energy from a particle in said interaction region between said first and second beams.

6. The particle detector as recited in claim 5 wherein said A/0 means is a Bragg cell.

7. The particle detector as recited in claim 5 wherein said optical means images said first and second beams through one portal in said enclosed volume and said detector means is positioned to detect forward scattered energy originating at said interaction region as it passes outside said enclosed volume through another portal.

8. The particle detector as recited in claim 5 wherein interference between said first and second beams at said interaction regions is manifested by a fringe pattern whose fringe edges move in accordance with said frequency f, whereby a particle passing through said interaction region creates a Doppler tone burst whose frequency is dependent upon the rate of movement of said particle through said interaction region.

9. The particle detector as recited in claim wherein said processing means includes filter means for isolating said Doppler tone burst and threshold means for determining if the envelope of said Doppler tone burst exceeds a pre-established limit.

10. The particle detector as recited in claim 9 wherein said processor means further includes a pair of parallel-connected mixers, each receiving said electrical signal, and local oscillator means for applying signals of frequency f displaced from each other by 90° to said mixers, and further means for summing the outputs of said mixers to produce a smoothed Doppler tone burst envelope for application to said threshold means.

11. A particle detector for detecting particles within an enclosed volume, said detector comprising:
laser means for producing a polarized optical beam and directing it along a path;
polarizing beam splitting means in said path for dividing said polarized optical beam into first and second linearly polarized beams
quarter wave means for altering the linear polarization of said first beam into a circular polarization of first helicity and directing said altered first beam into said volume to interact with a particle and acquire a resultant Doppler shifted light burst, said quarter wave means responsive to back scattered optical energy of opposite helicity originating from said first beam's interaction with said particle, to alter said back scattered optical energy to a linear polarization having a polarization vector orthogonal to a direction of polarization of said second beam, and to direct said linearly polarized back scattered optical energy to said polarizing beam splitter for combination with said second beam;
polarizing beam splitting means positioned in the path of said combined second beam and back scattered optical energy, and having orthogonal axes oriented at an angle with respect to the orthogonal polarization states of said combined second beam and back scattered optical energy: and
optical detection means responsive to a pair of beams emanating from said polarizing beam splitting means for detecting the presence of a Doppler shift in said beams which indicates the presence of a particle in said enclosed volume..

12. The particle detector as recited in claim 11 further comprising an internally reflective retro reflector associated with said polarizing beam splitting means and positioned in the path of said second beam, to direct said second beam back through said polarizing beam splitter for combination with said back scattered optical energy, said retro reflector rotatable so as to enable a change in orientation of the polarization state of said second beam.

13. The particle detector as recited in claim 11 wherein said optical detection means includes filter means for isolating said Doppler tone burst and threshold means for determining if the envelope of said Doppler tone burst exceeds a pre-established limit.

14. The particle detector as recited in claim 11 wherein the axes of said polarizing beam splitting means are oriented at a 45° rotational offset from the orthogonal polarization states of said combined second beam and back scattered optical energy.

15. The particle detector as recited in claim 14 wherein said optical detection means includes a photo detector for each said beam from said polarizing beam splitting means, one said photo detector providing a signal indicative of a subtraction of optical energies parallel to one axis of said polarizing beam splitting means and a second said photo detector providing a signal indicative of an addition of optical energies parallel to an orthogonal axis of said polarizing beam splitting means.

16. The particle detector as recited in claim 15 further comprising:
means for deriving a sample signal from said laser means and subtracting said signal from signals produced by said photo detection to reduce laser noise included therein.

* * * * *

UNITED STATES PATENT AND TRADEMARK OFFICE
CERTIFICATE OF CORRECTION

PATENT NO. : 5,192,870
DATED : 3/9/93
INVENTOR(S) : Batchelder et al.

It is certified that error appears in the above-identified patent and that said Letters Patent is hereby corrected as shown below:

```
Col. 8, line 12, Claim 2, after "claim" insert --1--.
Col. 8, line 18, Claim 3, after "claim" insert --2--.
Col. 8, line 27, Claim 4, "A/O" should read --A/0--.
Col. 8, line 37, Claim 4, "A/O" should read --A/0--.
Col. 8, line 54, Claim 5, after "claim" insert --4--.
Col. 8, line 59, Claim 6, "A/O" should read --A/0--.
Col. 9, line 6, Claim 9, after "claim" insert --8--.
```

Signed and Sealed this

Twenty-third Day of November, 1993

Attest:

BRUCE LEHMAN

Attesting Officer     Commissioner of Patents and Trademarks